(12) United States Patent
Khullar et al.

(10) Patent No.: US 9,173,848 B2
(45) Date of Patent: Nov. 3, 2015

(54) SOLID PHARMACEUTICAL FIXED DOSE COMPOSITIONS COMPRISING IRBESARTAN AND AMLODIPINE, THEIR PREPARATION AND THEIR THERAPEUTIC APPLICATION

(75) Inventors: Praveen Khullar, Goa (IN); Vinay Kolhe, Goa (IN); Amol Kulkarni, Goa (IN); Shirishbhai Patel, Goa (IN); Yashwant Phadke, Goa (IN); D Saravanan, Goa (IN); Mansing Shingte, Goa (IN)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/381,534

(22) PCT Filed: Sep. 17, 2009

(86) PCT No.: PCT/IB2009/007027
§ 371 (c)(1),
(2), (4) Date: Mar. 21, 2012

(87) PCT Pub. No.: WO2011/001202
PCT Pub. Date: Jan. 6, 2011

(65) Prior Publication Data
US 2012/0171288 A1    Jul. 5, 2012

(30) Foreign Application Priority Data
Jun. 30, 2009 (IN) .......................... 1341/DEL/2009

(51) Int. Cl.
*A61K 31/44* (2006.01)
*A61P 9/12* (2006.01)
*A61K 9/28* (2006.01)
*A61K 9/14* (2006.01)
*A61K 9/20* (2006.01)
*A61K 9/24* (2006.01)
*A61K 9/50* (2006.01)
(Continued)

(52) U.S. Cl.
CPC .............. *A61K 9/2077* (2013.01); *A61K 9/209* (2013.01); *A61K 9/5047* (2013.01); *A61K 9/5084* (2013.01); *A61K 31/4178* (2013.01); *A61K 31/4422* (2013.01)

(58) Field of Classification Search
None
See application file for complete search history.

(56) References Cited

U.S. PATENT DOCUMENTS

| 5,994,348 | A  | * | 11/1999 | Ku et al. ..................... | 514/223.5 |
| 2005/0143435 | A1 | * | 6/2005 | Baum et al. .................... | 514/381 |
| 2005/0250838 | A1 | * | 11/2005 | Challapalli et al. ........... | 514/419 |

FOREIGN PATENT DOCUMENTS

| WO | WO2005/070462 | A2 |   | 8/2005 |
| WO | WO2006/034631 | A1 |   | 4/2006 |
| WO | WO-2008-044862 |    | * | 4/2008 |

(Continued)

OTHER PUBLICATIONS

Database WPI Week 200627, Thomson Scientific, London, GB; AN, 2006-263482, XP002581681.

(Continued)

*Primary Examiner* — Ernst V Arnold
*Assistant Examiner* — Jianfeng Song
(74) *Attorney, Agent, or Firm* — Morrison & Foerster LLP (57) ABSTRACT

The present invention is directed to solid stable pharmaceutical fixed dose compositions comprising irbesartan, amlodipine besilate and pharmaceutically acceptable excipients, to their preparation and to their therapeutic application.

21 Claims, 2 Drawing Sheets

(51) Int. Cl.
*A61K 31/4178* (2006.01)
*A61K 31/4422* (2006.01)

(56) References Cited

FOREIGN PATENT DOCUMENTS

WO    WO2008/044862  A1    4/2008
WO    WO-2008044862    *    4/2008

OTHER PUBLICATIONS

International Search Report dated May 25, 2010 issued in PCT/IB2009/007027.
International Preliminary Report on Patentability dated Jan. 4, 2012 issued in PCT/IB2009/007027.

* cited by examiner

SOLID PHARMACEUTICAL FIXED DOSE COMPOSITIONS COMPRISING IRBESARTAN AND AMLODIPINE, THEIR PREPARATION AND THEIR THERAPEUTIC APPLICATION

This application claims priority PCT International Application Serial No. PCT/IB2009/007027, filed Sep. 17, 2009, which claims priority to Indian Patent Application No. 1341/DEL/2009, filed Jun. 30, 2009

FIELD OF THE INVENTION

The present invention is directed to solid stable pharmaceutical fixed dose compositions comprising irbesartan, amlodipine besilate and pharmaceutically acceptable excipients, to their preparation and to their therapeutic application.

BACKGROUND OF THE INVENTION

Amlodipine is a calcium channel blocker developed for the treatment of hypertension and other medical indications as disclosed in U.S. Pat. No. 4,572,909 and U.S. Pat. No. 4,879,303. Its chemical name is 3-ethyl-5-methyl-(++2-[(2-aminoethoxy)methyl]-4-(2-chlorophenyl)-1,4-dihydro-6-methylpyridine-3,5-dicarboxylate.

Amlodipine is marketed as the monobenzenesulfonate salt, amlodipine besylate under the trade name Norvasc® or Istin®. It is available as oral tablets in strengths of 2.5 mg, 5 mg and 10 mg. The inactive ingredients in the Norvasc® tablets include microcrystalline cellulose, dibasic calcium phosphate anhydrous, sodium starch glycolate and magnesium stearate.

Amlodipine besylate is slightly soluble in water and has an absolute bioavailability of 64-90%.

Irbesartan is described in Bernhart et al., U.S. Pat. No. 5,270,317, incorporated herein by reference.

Irbesartan, is a potent, long-acting angiotensin II receptor antagonist which is particularly useful in the treatment of cardiovascular ailments such as hypertension and heart failure. Its chemical name is 2-n-butyl-4-spirocyclopentane-1-[(2'-(tetrazol-5-yl)biphenyl-4-yl)methyl]-2-imidazolin-5-one.

Irbesartan is marketed by under the trade name Aprovel® or Karvea®.

Irbesartan is insoluble in water. Irbesartan has a parabolic pH solubility profile in aqueous medium with minimum solubility between pH 2.0 and 6.0 and maximum solubility in 0.1 N HCl and pH 7.5 phosphate buffer.

It is often desirable to combine multiple active ingredients in a single pharmaceutical composition. Inclusion of multiple ingredients in a single composition generally reduces costs and provides the convenience of consuming a single medication rather than multiple medications for treating individual symptoms.

However, a combination of active ingredients is not without drawbacks.

Certain physical properties of the drugs and specifically stability, present a challenge in developing formulations suitable for preparing a tablet having reduced levels of total impurities on long term stability.

Irbesartan is, for example, a fluffy material, with relatively low bulk and tap densities. It is also a sticky and abrasive material.

These properties make it difficult to formulate an effective amount of the drug into a small tablet with uniformity of weight, hardness, and other desirable tablet properties. In addition, irbesartan has certain undesirable flow characteristics, for example, is sticky and can adhere to surfaces such as tablet punch faces and dies, causing problems in tableting, especially on a high speed tablet press.

The very low aqueous solubility of irbesartan also presents a challenge, since only limited amounts of excipients may be added to facilitate wetting, disintegration, and ultimately, rapid and complete drug release.

The addition of a second active ingredient such as amlodipine besilate, which is also a fluffy material exhibiting poor flow and low aqueous solubility, can further contribute to problems such as tableting or uniformity of dosage units.

In addition, the stability of a composition might be compromised due to incompatibility of an active with an essential excipient or even between a second active itself.

Concerning formulations containing Amlodipine besilate alone, WO 2006/059217 discloses that amlodipine is highly hygroscopic and absorbs moisture, which leads to degradation. One of the major routes of degradation is via a catalytic oxidative process, which is pH dependent. One of the major degradation products known in the art is 3-ethyl-5-methyl-2-[(2-aminoethoxy)methyl]-4-(2-chlorophenyl)-6-methylpyridine-3,5-dicarboxylate and called Impurity D.

WO2003/051364 discloses Amlodipine besilate tablets with improved stability of the active ingredient and reduced in weight containing microcrystalline cellulose, a lubricant and a disintegrating agent and the process for the preparation of said tablets.

WO2008/062435 discloses a stable solid dosage form of amlodipine besylate comprising polyols and having reduced levels of total impurities on stability and especially impurity D.

Concerning formulations containing Irbesartan, EP747050 from Sanofi discloses pharmaceutical composition under tablets comprising Irbesartan alone or in combination with a diuretic compound such as Hydrochlorothiazide (HCTZ) prepared by a process comprising mixing an extragranular composition with granules comprising either irbesartan alone or the two active principles in the presence of lactose and an antiadherent such as silicon dioxide. No problem of stability is raised.

WO2005/070762 from Sepracor discloses oral formulation under capsules comprising the combination of S-amlodipine and Irbesartan obtained by simple mixing about 25 wt % of the two active principles together in the presence of corn starch and about 65 wt % of lactose. No problem of stability is raised.

Thus, there is no known stable solid dosage form comprising the specific combination of Irbesartan and Amlodipine besilate.

In addition to stability, when formulating solid fixed dose combination, the objective is to provide a patient-convenient combination dosage form of active ingredients that is bioequivalent to the corresponding free-combination of the same active ingredients.

As used herein, "fixed-dose-combination or FDC" refers to a combination of two drugs or active ingredients presented in a single dosage unit such as a tablet or oral dosage form.

Further as used herein, "free-combination" refers to a combination of two drugs or active ingredients dosed simultaneously but as two dosage units.

As a result of these complex biopharmaceutical properties, development of a fixed-combination dosage form of irbesartan and amlodipine besilate that is bio equivalent to a free-combination thereof is challenging.

Accordingly, a fixed-combination solid dosage formulation of Irbesartan and amlodipine besilate that is stable and bioequivalent to the corresponding free-combination would be desirable.

One other challenge faced is homogenity of Amlodipine in a lubricated blend as the content of Amlodipine in the total tablet weight should be very low compared to the high amount of irbesartan.

The object of the present invention is to alleviate at least partly the above mentioned drawbacks.

SUMMARY OF THE INVENTION

This object is achieved with a stable solid oral pharmaceutical fixed dose composition comprising irbesartan, amlodipine besilate and pharmaceutically acceptable excipients, wherein irbesartan is physically separated from amlodipine besilate.

This solid dosage form is particularly advantageous since amlodipine besilate does not undergo degradation and this combination product shows reduced and controlled impurities even lesser than with regards to individual reference products of same dose when subjected to stress studies and in finished pack.

In addition, the dissolution profile of both irbesartan and amlodipine besilate is not compromised by comparison to the dissolution profile of each active ingredient alone.

In a preferred embodiment, irbesartan under the form of coated granules is embedded in an extragranular matrix comprising amlodipine besilate.

Preferably the solid composition of the invention takes the form of a monolayer tablet, preferably film coated Preferably, the tablet is further package in suitable packing material such as PVC, PVC/PVdC, PVC/PE/PVdC.

In a preferred embodiment of the composition according to invention, the irbesartan represents between about 20% and about 70% by weight of the total composition.

In a preferred embodiment of the composition according to invention the amlodipine besilate represents between about 1% and about 20% by weight of the total composition.

In a preferred embodiment of the composition according to invention the pharmaceutically acceptable excipients are selected from the group consisting of diluent, disintegrant, antiadherent, binder lubricant and mixture thereof.

Preferably said solid composition is free of lactose.

In a preferred embodiment of the composition according to invention the amount of Irbesartan is comprised between 150 mg and 300 mg of the total weight of the tablet, preferably 300 mg or 150 mg.

In a preferred embodiment of the composition according to invention the amount of amlodipine besilate is comprised between 5 mg and 10 mg of the total weight of the tablet, preferably 7 mg or 14 mg.

In a preferred embodiment of the composition according to invention the solid composition is under the form of a tablet wherein the total weight of the tablet is between 400 mg and 600 mg, preferably 500 mg.

In a preferred embodiment the composition has less than 1.50% (w/w) of total impurities for Amlodipine and less than 0.50% (w/w) of total impurities for Irbesartan after 6 months at 40° C./75% RH.

According to another object, the invention is related to a process for the preparation of a stable oral pharmaceutical composition comprising irbesartan and amlodipine besilate, wherein the process comprises the steps of:

i. granulating irbesartan and one or more pharmaceutically acceptable excipients, with aqueous solution containing a binder, to form granules,
ii. drying the granules;
iii. separately blending amlodipine besilate with pharmaceutically acceptable excipients,
iv. mixing the irbesartan granules of step ii with the amlodipine besilate blend of step iii);
v. lubricating the blend of step iv); optionally after a pre-lubricating step; and
vi. compressing the mixture into tablets.

Preferably, the group of pharmaceutically acceptable excipients used in step I and iii) of the process is free of lactose.

In a preferred embodiment of the process further comprises the step of coating the tablet and packaging in suitable packing material such as PVC, PVC/PVdC, PVC/PE/PVdC.

Preferably the pre-lubricating step comprises the mixing of the blend of step (iv) during 10 to 25 nm, preferably 20 nm before doing the lubricating step.

According to another object, the invention is related to the use of Irbesartan and amlodipine besilate in the manufacture of a medicament for the treatment of hypertension wherein said medicament is in the stable solid fixed dose composition as described above Preferably, the use referred to a second line treatment for hypertensive patients not sufficiently controlled using amlodipine as Calcium Chanel Blockers (CCB) monotherapy or irbesartan as angiotensin II receptor antagonist (ARB).

DETAILED DESCRIPTION OF THE INVENTION

Preferred Irbesartan and Amlodipine Besilate Compositions.

The two actives are present in a single unit dosage form, such as tablets or pellets, wherein irbesartan is physically separated from amlodipine besilate.

Pharmaceutically acceptable additives suitable for use in the present invention with amlodipine besylate are selected from suitable diluents such as microcryastalline cellulose, di calcium phosphate and suitable lubricants such as magnesium stearate.

Pharmaceutically acceptable additives suitable for use in the present invention with Irbesartan are selected from suitable diluents such as Microcrystalline cellulose, suitable glidants such as silicone dioxide, suitable lubricants such as magnesium sterate, suitable binders such as hypromellose.

In the composition of the invention, Amlodipine portion composition is similar to the reference composition of Amlodipine formulation Norvasc® and Irbesartan portion is similar to the reference composition of Approvel® except without Lactose monohydrate.

In a preferred embodiment, the composition is free of lactose as diluent. Indeed the absence of this excipient allows achieving best results in term of global stability of amlodipine besilate and specifically lowering the amount of impurity D.

In a preferred form of the tablet, irbesartan is present under the form of coated granules embedded in an extragranular matrix comprising amlodipine besilate along with excipients. Irbesartan is granulated with a binder such as HPMC for facilitating granulation and amlodipine is added in the extragranular portion before compression step.

In another preferred form, irbesartan and amlodipine are both separately granulated using respective suitable binder before blending with lubricants and further compression.

Thus the solid composition takes the form of a monolayer tablet, preferably film coated.

In another preferred form, irbesartan granules and amlodipine granules along with excipients are separated by an inert layer. Thus the solid composition takes the form of a trilayer tablet, preferably film coated. In that embodiment the inert layer preferably comprises suitable diluent.

The preferred form is a monolayer form wherein a physical barrier is placed around the irbesartan active ingredient. The physical barrier serves to reduce or eliminate the physical contact between irbesartan as the protected active ingredient and amlodipine besilate, the other active ingredients of the combination.

Preferred compositions of the present invention contain one or more of the following components in the indicated concentration range (% by weight): irbesartan, 50 to 70% most preferably, 60%, amlodipine besilate, 1 to 10%, most preferably 2 to 6%, diluent, 20 to 30%, most preferably about 25%, binder, 1 to 5%, most preferably 2 to 3%; disintegrant, 3 to 6%, most preferably about 5%; antiadherent or glidant, 0.25 to 5.0% most preferably 0.7 to 2%, lubricant, 0.5 to 1.5, most preferably about 1%.

The amount of each ingredient (active and additives) in the solid dosage formulation of the invention may specifically vary within the following ranges.

| | | Total % Content in the formulation | | |
|---|---|---|---|---|
| Component | 150/5 mg strength | 150/10 mg strength | 300/5 mg strength | 300/10 mg strength |
| | Intragranular | | | |
| 1 Irbesartan | 60.00 | 60.00 | 60.00 | 60.00 |
| 2 Diluent | 26.40 | 21.60 | 26.40 | 26.40 |
| 3 disintegrant | 4.80 | 4.80 | 480 | 4.80 |
| 4 binder | 2.00 | 2.00 | 2.00 | 2.00 |
| 5 Purified water | q.s. | q.s. | q.s. | q.s. |
| | Extragranular | | | |
| 6 Amlodipine Besilate equivalent to Amlodipine | 2.80 | 5.60 | 1.40 | 2.80 |
| 7 diluent | 2.00 | 4.00 | 3.40 | 2.00 |
| 8 Antiadherent or glidant | 1.00 | 1.00 | 1.00 | 1.00 |
| 9 lubricant | 1.00 | 1.00 | 1.00 | 1.00 |
| 10 Coating material | 4.00 | 4.00 | 4.00 | 4.00 |

Particle size distribution of Irbesartan is important because the fines of Irbesartan granules help for uniformity of Amlodipine. The particle size distribution of Irbesartan granules mainly depends on fluid uptake during granulation and kneading time. The preferred size distribution of Irbesartan granules is in the range of 65 to 85% passing through #60 BSS, i.e. having a size or a diameter less than 250 μm.

The final pH observed for the Irbesartan and Amlodipine formula composition of the invention is around 6.0, where as pH of individual reference product was found to be higher than 6.0 i.e. in between pH 6.0 to 7.0. The Amlodipine composition favors pH above 6, but below pH 6.0 the degradation process of amlodipine accelerates.

Hence in the present invention the selected compositions can attain pH 6 when compressed into tablets.

The final primary packaging material used is blister packaging i.e. Opaque Triplex (300micPVC/30micPE/90gsmPVdC), Opaque duplex (250micPVC and 60 mic PVdC) and Alu-Alu blister packs. These materials will avoid increasing generation of Impurity-D in amlodipine thereby inhibiting direct exposure of sun light on drug product.

The main impurity to be controlled in the composition of the invention is Impurity D known in the art as 3-ethyl-5-methyl-2-[(2-aminoethoxy)methyl]-4-(2-chlorophenyl)-6-methylpyridine-3,5-dicarboxylate.

In the compositions according to the invention, less than 1.5% (w/w) of total impurities for Amlodipine is found after 6 months at 40° C./75% RH, but more than 1.6% of impurity is found when irbesartan and amlodipine are not physically separated. In a preferred embodiment less than 1.0% and more preferably less than 0.5% (w/w) of total impurities for Amlodipine is found in the composition of the invention after 6 months at 40° C./75% RH.

In addition less than 1.5% (w/w) [actual 0.097% w/w] of Impurity D for Amlodipine is found after 6 months at 40° C./75% RH in the compositions according to the invention, but more than 1.6% of impurity D is found when Irbesartan and amlodipine are not physically separated. In a preferred embodiment less than 1.0% and more preferably less that 0.15% (w/w) of impurity D for Amlodipine is found in the composition of the invention after 6 months at 40° C./75% RH.

This shows that the specific compositions of the invention have a lowering impact on the degradation profile of amlodipine besilate.

On the other side less than 0.5% (w/w) of total impurities for irbesartan is found after 6 months at 40° C./75% RH. This shows that the specific composition of the invention have no impact on the degradation profile of Irbesartan. In addition, there is no change in the physical properties of tablets such as color, shape, hardness, and disintegration time.

Physical Properties.

Stability Performances.

The oral pharmaceutical compositions of the present invention were subjected to accelerated stability studies at the following conditions; 40° C./75% relative humidity RH, 30° C./75% RH and 25° C./60% RH. These were evaluated on the basis of assay, in vitro dissolution, moisture content and related substances measured between initial and 6-months time points for irbesartan as well as amlodipine besilate.

The results provide a significant decrease in the total impurity levels in Amlodipine mainly Imp D when Irbesartan and Amlodipine both are physically separated.

Specifically, it was found that impurity levels in the Amlodipine is quite low and within the target limit in the formula where Irbesartan granulated and Amlodipine was added in the extragranular portion. This composition shows impurity levels much lower than that of reference products.

Dissolution Performances.

The "dissolution performance" of a tablet containing the combination of Irbesartan and amlodipine besilate is compared to the dissolution performance of each reference product in multimedia dissolution conditions such as 0.1 N HCl, pH 4.5 Acetate buffer, pH 6.8 phosphate buffer and pH 7.5 phosphate buffer. The progress of dissolution is monitored at various time points between initial point and 60 minutes.

Figure 1:
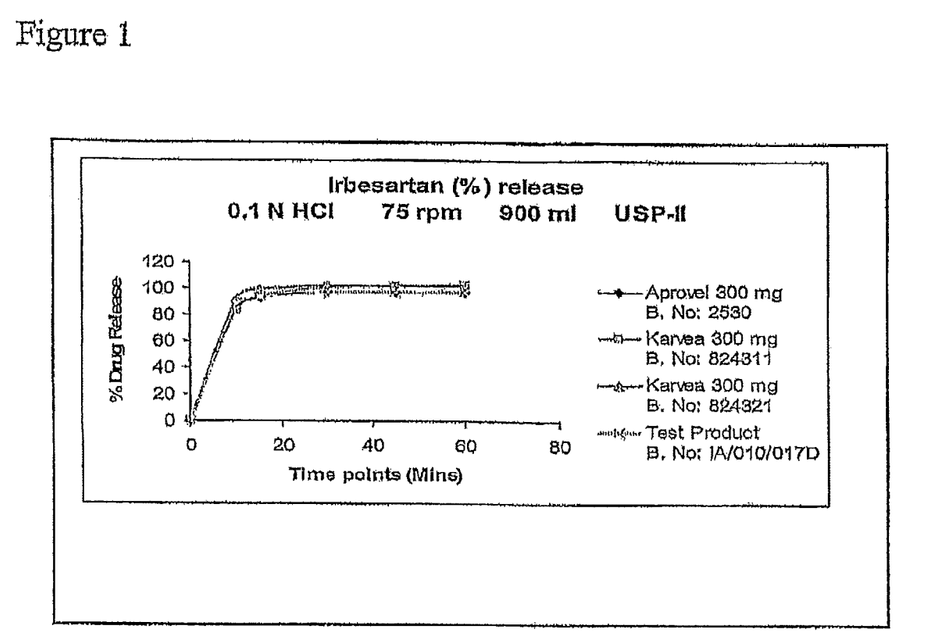
FIG. 1 shows the dissolution profile of Irbesartan in routine media i.e. 0.1 N HCl.
Figure 2:
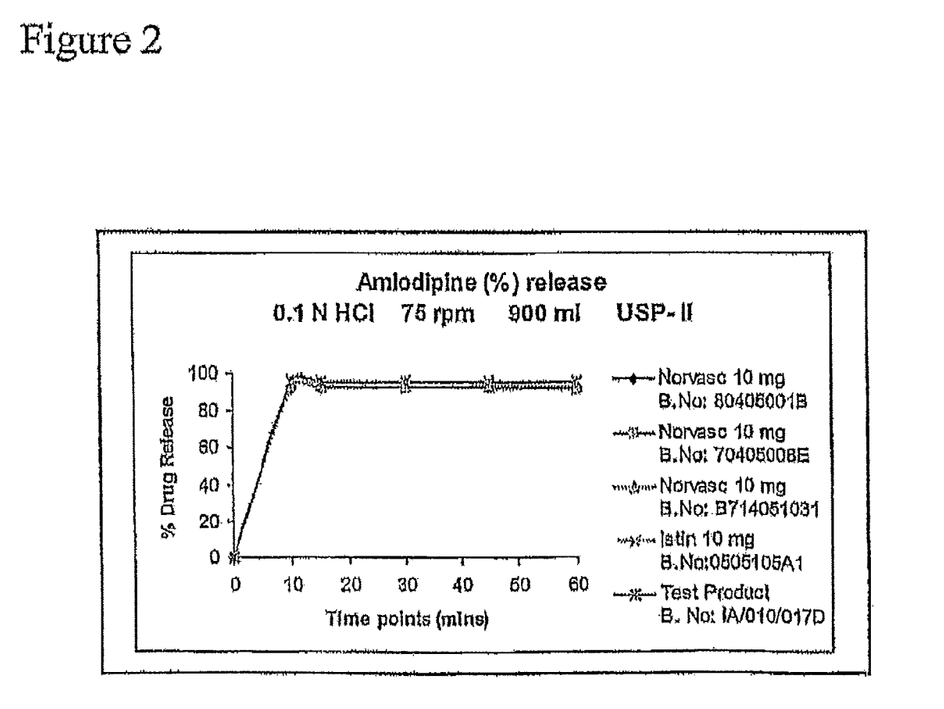
FIG. 2 shows the dissolution profile of amlodipine in routine media i.e. 0.1 N HCl.

The dissolution profiles refers to the weight % of irbesartan or amlodiopine release, based on the total weight of irbesartan or amlodipine contained in the tablet, which dissolves within 60 minutes under the different multimedia conditions (see FIGS. 1 and 2 for routine media i.e. 0.1 N HCl).

The results show that the dissolution performances of the tablet containing the combination of irbesartan and amlodipine besilate of the invention are equivalent to the dissolution performances of the tablets containing each active ingredient irbesartan or amlodipine alone.

Method of Manufacture.

The process for the preparation of a stable oral pharmaceutical composition comprising irbesartan and amlodipine besilate, comprises the following steps:

i. granulating irbesartan and one or more pharmaceutically acceptable excipients with aqueous solution containing a binder to form granules, Preferably acceptable excipients are selected from the group consisting of microcrystalline cellulose, croscarmelose sodium. Preferably acceptable binder, are selected from the group consisting of cellulose derivatives such as hydroxypropyl methylcellulose.

ii. drying the granules;

iii. separately blending amlodipine besilate with pharmaceutically acceptable excipients for better uniform distribution of Amlodipine. Preferably acceptable excipients are selected from the group consisting of microcrystalline cellulose, silicon dioxide.

iv. mixing the irbesartan granules of step i) with the amlodipine besilate blend of step iii);

v. lubricating the blend of step iv); optionally after a pre-lubricating step; and vi. compressing the mixture into tablets.

In a preferred embodiment of the process, a pre-lubricating step is carried on before step v) in order to achieve good homogenity for both Irbesartan and Amlodipine. Preferably the pre-lubricating step comprises the mixing of the blend of step (iv) during 10 to 25 nm, preferably 20 nm before doing the lubricating step.

Indeed, since the Irbesartan is present in the intragranular portion and Amlodipine is mixed with other extragranular excipients like Microcrystalline Cellulose and silicon dioxide, homogeneous distribution of Amlodipine in the final blend is necessary.

Hence, proper mixing of intragranular and extragranular material is important stage to achieve homogeneity of Amlodipine in the final blend, which can be done during prelubrication step by mixing Irbesartan granules with extragranular material till the content uniformity for Amlodipine is achieved, between 90 to 110% of the label claim with RSD (Relative standard deviation) less than 5%, which revealed the uniform distribution of Amlodipine Besilate in the lubricated blend.

In a preferred embodiment, the group of pharmaceutically acceptable excipients used in the process is free of lactose.

The process further comprises the step of coating the tablet and packaging preferably in opaque triplex blister pack.

Efficacy Performance.

An object of the invention is the use of the composition of the invention containing Irbesartan and amlodipine besilate in the manufacture of a medicament for the treatment of hypertension wherein said medicament is in stable solid fixed dose compositions as described above.

In a preferred embodiment, the compositions of the invention are administered to patient having a mild to moderate hypertension, as second line treatment for hypertensive patients not sufficiently controlled on amlodipine (Calcium Chanel Blockers CCB) or irbesartan (angiotensin II receptor antagonist ARB) monotherapy.

Phase III, double-blind, randomized, placebo-controlled, 8-week partial factorial was designed to evaluate the combinations of Irbesartan 150 mg/Amlodipine 5 mg and Irbesartan 300 mg/Amlodipine 5 mg tablets versus Amlodipine 5 mg, Irbesartan 150 mg and 300 mg monotherapy, after 8 weeks of treatment in patients with uncomplicated primary essential hypertension.

This study aims to demonstrate that the antihypertensive efficacy of the fixed dose composition Ibesartan and amlodipine 150/5 mg or 300/5 mg is superior to the corresponding dose of monotherapy of amlodipine or irbesartan.

The invention has been described with reference to preferred embodiments. However, many variations are possible within the scope of the invention.

EXAMPLES

C1, C2, C3 represent comparative formulations. I1, I2, I3 represent formulations of the invention wherein irbesartan is physically separated from amlodipine.

Aprovel® 300 mg Karvea® 300 mg represents formula C1 as reference product for Irbesartan alone.

Istin 10 mg or Norvasc® 10 mg represents formula C2 as reference product for Amlodipine besilate alone.

Example 1

Preparation of Composition C3 Wherein Irbesartan and Amlodipine are Both Granulated Together

TABLE 1

| Name of ingredients | Quantity (mg/tab) |
|---|---|
| Intragranular Phase | |
| Irbesartan | 300.00 |
| Amlodipine Besilate | 14.00 |
| Microcrystalline Cellulose | 142.00 |
| Croscarmellose Sodium | 24.00 |
| Hypromellose | 10.00 |
| Purified Water # | q.s |
| Extra granular Phase | |
| Colloidal Silicon Dioxide | 5.00 |
| Magnesium Stearate | 5.00 |
| Total weight of core tablet (mg) | 500.00 |
| Opadry white II | 10.00 |
| Total weight of coated tablet (mg) | 510.00 |

This formula C3 may be prepared by any suitable granulation process known in the art.

Example 2

Preparation of Composition of the Invention I1 Wherein Irbesartan is in the Intragranular Portion and Amlodipine is Added in the Extragranularly This combination is also referenced under Test product.

TABLE 2

| Step. No. | Component | Function | (%) Qty/unit | Quantity/unit (mg) 150mg/10mg | 300mg/10mg |
|---|---|---|---|---|---|
| Internal Phase | | | | | |
| 1. | Irbesartan | Active substance | 60.00 | 150.00 | 300.00 |
| 2. | Microcrystalline Cellulose (Avicel PH 101) | Diluent/Binder | 26.40 | 66.00 | 132.00 |
| 3. | Croscarmellose sodium | Disintegrant | 4.80 | 12.00 | 24.00 |

TABLE 2-continued

| Step. No. | Component | Function | (%) Qty/unit | Quantity/unit (mg) 150mg/10mg | Quantity/unit (mg) 300mg/10mg |
|---|---|---|---|---|---|
| 4. | Hypromellose (HPMC 6 cps) | Binder | 2.00 | 5.00 | 10.00 |
| 5. | Purified water [a] | Solvent for granulation | q.s. | q.s. | q.s. |
| | | External Phase | | | |
| 6. | Amlodipine Besylate equivalent to Amlodipine | Active substance | 2.80 | 7.00 5.00 | 14.00 10.00 |
| 7. | Microcrystalline Cellulose (Avicel PH 112) | Diluent | 2.00 | 5.00 | 10.00 |
| 8. | silicon dioxide | Glidant/antiadherent | 1.00 | 2.50 | 5.00 |
| 9. | Magnesium stearate | Lubricant | 1.00 | 2.50 | 5.00 |
| Core Tablet Weight | | | 100% | 250 mg | 500 mg |
| 10. | Opadry White 03B28796 [b] | Coating agent | 4.00 | 10.00 | 20.00 |
| 11. | Purified water [a] | Solvent for coating | q.s. | q.s. | q.s. |
| Coated Tablet Weight | | | | 260 mg | 520 mg |

Extragranulation Process of Manufacturing the Combination of Irbesartan and Amlodipine Besilate Under Tablet According to Formula I1.

Step-1: Mix Irbesartan, Microcrystalline cellulose and Croscarmellose sodium in raped mixer granulator.

Step-2: Granulate the dry mix of step 1 with aqueous solution of hypromellose.

Step-3: Dry the wet granules and mill the dried granules through 1.00 to 2.00 mm screen.

Step-4: Add extragranular material i.e. Amlodipine Besilate, Microcrystalline Cellulose and Silicone dioxide and mix in a low shear blender.

Step-5: Add Magnesium Stearate to step 4 material and mix in a low shear blender.

Step-6: Compress the lubricated blend using suitable toolings.

Step-7: Finally coat the compressed tablets to achieve 2-4% of weight gain.

Example 3

Preparation of Composition of the Invention I2 Wherein Irbesartan and Amlodipine Besilate are Physically Separated by Both Separate Granulations

TABLE 3

| Step. No. | Name of ingredients | Quantity (mg/tab) |
|---|---|---|
| | Irbesartan Granulation | |
| 01 | Irbesartan | 300.00 |
| 02 | Microcrystalline Cellulose | 50.00 |
| 03 | Croscarmellose Sodium | 20.00 |
| 04 | Hypromellose | 7.00 |
| 05 | Purified Water # | q.s |
| | Amlodipine Besilate Granulation | |
| 06 | Amlodipine Besilate | 14.00 |
| 07 | Povidone K 30 | 9.00 |
| 08 | Calcium Hydrogen Phosphate | 60.00 |
| 09 | Microcrystalline Cellulose | 40.00 |
| 10 | Crospovidone | 6.00 |
| 11 | Purified Water # | q.s |

TABLE 3-continued

| Step. No. | Name of ingredients | Quantity (mg/tab) |
|---|---|---|
| | Extragranular Phase | |
| 12 | Microcrystalline Cellulose | 10.00 |
| 13 | Colloidal Silicon Dioxide | 5.00 |
| 14 | Magnesium Stearate | 5.00 |
| Total weight of core tablet (mg) | | 526.00 |
| 15 | Opadry white II | 10.00 |
| Total weight of coated tablet (mg) | | 536.00 |

Example 4

Preparation of Composition of the Invention I3 Under Tri-Layers Tablet Wherein Irbesartan Layer and Amlodipine Besilate Layer are Physically Separated by an Inert Layer

TABLE 4

| Step .N° | INGREDIENTS | Qty/Tab (mg) |
|---|---|---|
| | Irbesartan Layer - weight 500 mg | |
| 1. | Irbesartan | 300.0 |
| 2. | Lactose monohydrate | 102.0 |
| 3. | Microcrystalline cellulose | 54.0 |
| 4. | Croscarmellose sodium | 24.0 |
| 5. | Hypromellose | 10.0 |
| 6. | Purified water | qs |
| 7. | Colloidal silicon dioxide | 5.0 |
| 8. | Magnesium stearate | 5.0 |
| | Inert layer - weight 200 mg | |
| 9. | Microcrystalline cellulose | 169.75 |
| 10. | Partially pregelatinized starch | 30.0 |
| 11. | Iron oxide red (colorant) | 0.25 |
| | Amlodipine layer - weight 220 mg | |
| 12. | Amlodipine besilate | 14.0 |
| 13. | Povidone k 30 | 20.0 |
| 14. | Microcrystalline cellulose | 60.0 |

TABLE 4-continued

| Step .N° | INGREDIENTS | Qty/Tab (mg) |
|---|---|---|
| 15. | Crospovidone | 6.0 |
| 16. | Calcium hydrogen phosphate, anhydrous | 106.0 |
| 17. | Purified water | Qs |
| 18. | crospovidone | 11.0 |
| 19. | Magnesium stearate | 3.0 |
| | Average weight of the tablet | 920 mg |

Example 5

Stability Studies

The oral pharmaceutical compositions of the present invention were subjected to accelerated stability studies at the following conditions; 40° C./75% relative humidity RH, 30° C./75% RH and 25° C./60% RH. These were evaluated on the basis of assay, in vitro dissolution, moisture content and related substances measured between initial and 6-months time points for irbesartan as well as amlodipine besilate.

This test is carried on under the following conditions.

The tablets were packed in to the opaque triplex—alu blister pack and such blister were further packed in to the cartons, and cartons were charged on to the stability as per ICH guidelines, and samples were taken out at each stability stage interval and submitted for analysis.

The stability results at +40° C./75% RH are provided in table 5.

TABLE 5

| Ex. | Conditions | Total Impurities from irbesartan in % w/w of the total composition | Impurity-D from Amlodipine in % w/w of the total composition | | Total Impurities from amlodipine in % w/w of the total composition. | |
|---|---|---|---|---|---|---|
| | | 6 months | initial | 6 months | initial | 6 months |
| C1 | Irbesartan Aprovel 300 mg | 0.14 | NA | NA | NA | NA |
| C2 | Amlodipine besilate Test product Istin 10 mg | NA | 0.06 | 0.38 | 0.05 | 0.99 |
| C3 | Irbesartan + Amlodipine besilate COMBINED GRANULATION | 0.15* | 0.49* | 1.60* | 0.70* | 2.33* |
| I1 | Irbesartan + Amlodipine besilate SEPARATION by extragranulation Test product | 0.171 | 0.017 | 0.097 | 0.066 | 0.329 |
| I2 | Irbesartan + Amlodipine besilate SEPARATION by granulation | 0.08** | 0.06** | 0.16** | 0.15** | 0.33** |
| I3 | Irbesartan + Amlodipine besilate SEPARATION by triple layer | 0.034** | 0.026** | 0.188** | 0.046** | 0.388** |

*2 months
**3 months

The formulation containing both Irbesartan and Amlodipine granulated together shows higher level of imp D during stability studies at 40° C./75% RH at 2 months, hence further stability study was discontinued.

From the above results, it may be concluded that there is an increase in the total impurity levels in Amlodipine and mainly Imp D when Irbesartan and Amlodipine are granulated together.

When Irbesartan and Amlodipine both are physically separated it was found that impurity levels in the Amlodipine is quite low.

Hence formula II where Irbesartan granulated and Amlodipine was added in the extragranular portion shows the best results of impurity levels i.e. specifically much lower than that of reference products (Istin 10 mg).

In the compositions according to the invention I1, I2, I3, less than 1.5% (w/w) of total impurities for Amlodipine is found after 6 months at 40° C./75% RH, although more than 1.6% of impurity is found when irbesartan and amlodipine are not physically separated (C3). In a preferred embodiment less than 1.0% and more preferably less that 0.5% (w/w) of total impurities for Amlodipine is found in the composition of the invention (I1, I2, I3) after 6 months at 40° C./75% RH.

In addition less than 1.5% (w/w) of Impurity D for Amlodipine is found after 6 months at 40° C./75% RH in the compositions according to the invention (I1, I2, I3), although more than 1.6% of impurity D is found when irbesartan and amlodipine are not physically separated (C3). In preferred embodiments, less than 1.0% and more preferably less that 0.15% (w/w) of impurity D for Amlodipine is found in the composition of the invention (I1, I2, I3) after 6 months at 40° C./75% RH.

In a more preferred embodiment less that 0.15% (w/w) of impurity D for Amlodipine and less than 1.5% (w/w) of total impurities for Amlodipine is found after 6 months at 40° C./75% RH in the composition of the invention (I1).

This shows that the specific compositions of the invention have a lowering impact on the degradation profile of amlodipine besilate.

On the other side less than 0.5% (w/w) of total impurities for irbesartan is found after 6 months at 40° C./75% RH. This shows that the specific composition of the invention have no impact on the degradation profile of Irbesartan.

Example 4

Bioequivalence Dissolution Profiles

The dissolution profiles of the products of the invention are compared to the dissolution profiles of the references products. These studies are carried out per the multimedia dissolution profile study conditions established as followed.

The dissolution profiles were carried out with avg tablet weight of 260 mg [for 150/5 mg & 150/10 mg] or 520 mg [for 300/5 & 300/10 mg strength] of Irbesartan and Amlodipine FCT using USP apparatus II, placing a tablet in 900 ml of dissolution media at 37° C. and measuring the amount of Irbesartan or Amlodipine progressively dissolved [using HPLC, wavelength 240 nm] at different time points such as 10, 15, 30, 45 & 60 mins till the extend of 90% drug dissolves was achieved.

The results as illustrated in FIGS. 1 and 2 show that the dissolution performances of the tablet containing the combination of irbesartan and amlodipine besilate of the invention are equivalent to the dissolution performances of the tablets containing each active ingredient irbesartan or amlodipine alone.

Example 5

Clinical Studies Phase III

The fast study is conducted with the fixed combination of irbesartan and amlodipine 150/5 and 300/5 mg and with irbesartan 150 and 300 mg.

The combination therapy of irbesartan and amlodipine is expected to provide enhanced efficacy in patients not adequately controlled by irbesartan monotherapy alone.

The second study is conducted with the fixed combination of irbesartan and amlodipine 150/5 and 150/10 mg and with amlodipine 5 and 10 mg.

The combination therapy of irbesartan and amlodipine is expected to provide enhanced efficacy in patients not adequately controlled by irbesartan monotherapy alone.

The results will demonstrate that the antihypertensive effect as assessed by home blood pressure measurement (HBPM) of the fixed combination of irbesartan and amlodipine 150/5 mg is superior to that of amlodipine 5 mg alone in hypertensive patients insufficiently controlled by amlodipine 5 mg monotherapy.

244 patients are randomised in each clinical study. This will give 122 patients randomised and 103 patients for evaluation in each treatment group.

All the treatments were administrated orally, once daily in the morning.
Efficacy Criteria.

Home Blood pressure BP measurements is performed using for all patients the same validated automatic non invasive BP monitor according to a standard procedure: Twice a day for 7 days, 2 measurements in the morning and 2 measurements in the evening.

These HBPM periods are performed the week before V2, V3 and V4.

Office BP measurements are performed at each visit. All investigators are using the same validated automatic non invasive BP monitor.

Primary efficacy criterion: Home SBP as primary criterion is based on the measurements made by the patient for the last 7 days of each measurement period.

Morning and evening measurements of the first day of each measurement period are discounted in this criterion as they are considered as a training.

The primary criterion is calculated based on the average of all available measurements out of a maximum of 24 measurements (4 measurements per day for 6 days). This average is computed only if a minimum of 12 correct measurements are recorded over the last 6 days of each period of measurement.

From the first study, the results will demonstrate that the antihypertensive efficacy of the fixed combination irbesartan/amlodipine 300/5 mg is superior to that of irbesartan 300 mg monotherapy in lowering Systolic Blood Pressure assessed by home blood pressure measurement (HBPM) after 10 weeks of treatment (W10).

From the second study, the results will demonstrate that the antihypertensive effect as assessed by home blood pressure measurement (HBPM) of the fixed combination of irbesartan and amlodipine 150/5 mg is superior to that of amlodipine 5 mg alone in hypertensive patients insufficiently controlled by amlodipine 5 mg monotherapy.

The invention claimed is:

1. A stable solid oral pharmaceutical fixed dose composition in the form of a monolayer tablet comprising irbesartan, amlodipine besilate and pharmaceutically acceptable excipients, wherein the irbesartan is present as coated granules embedded in an extragranular matrix comprising amlodipine besilate, wherein the amlodipine besilate is not in granular form, and wherein the composition has less than 1.50% (w/w) of total impurities for amlodipine and less than 0.50% (w/w) of total impurities for irbesartan after 6 months at 40° C./75% relative humidity.

2. The composition according to claim 1, wherein the tablet is film coated.

3. The composition according to claim 2 wherein the tablet is further packaged in suitable packing material.

4. The composition according to claim 1 wherein the irbesartan represents between about 20% and about 70% by weight of the total composition.

5. The composition according to claim 1 wherein the amlodipine besilate represents between about 1% and 20% by weight of the total composition.

6. The composition according to claim 1 wherein the pharmaceutically acceptable excipients are selected from the group consisting of diluent, disintegrant, antiadherent, binder, lubricant, and mixtures thereof.

7. The composition according to claim 1 wherein said solid composition is free of lactose.

8. The composition according to claim 1 wherein the amount of irbesartan is between 150 mg and 300 mg of the total weight of the tablet.

9. The composition according to claim 1 wherein the amount of amlodipine besilate is between 5 mg and 10 mg of the total weight of the tablet.

10. The composition according to claim 1 in the form of a tablet wherein the total weight of the tablet is between 400 mg and 600 mg.

11. A process for the preparation of the composition of claim 1, wherein the process comprises the steps of:
   i. granulating irbesartan and one or more pharmaceutically acceptable excipients with aqueous solution containing a binder to form granules;
   ii. drying the granules;
   iii. separately blending amlodipine besilate with pharmaceutically acceptable excipients;
   iv. mixing the irbesartan granules of step iii with the amlodipine besilate blend of step iii;
   v. lubricating the blend of step iv), optionally after a pre-lubricating step; and
   vi. compressing the mixture into tablets.

12. The process according to claim 11 wherein the group of pharmaceutically acceptable excipients used in step i) and iii) of the process is free of lactose.

13. The process according to claim 11 further comprising the step of coating the tablet and packaging in suitable packing material.

14. The process according to claim 11 wherein the pre-lubricating step comprises the mixing of the blend of step iv) 10 to 25 min before doing the lubricating step.

15. The composition according to claim 3 wherein said suitable packing material is PVC, PVC/PVdC or PVC/PE/PVdC.

16. The composition according to claim 1 wherein the amount of irbesartan is 300 mg of the total weight of the tablet.

17. The solid composition according to claim 1 wherein the amount of irbesartan is 150 mg of the total weight of the tablet.

18. The solid composition according to claim 1 wherein the amount of amlodipine besilate is 7 mg.

19. The solid composition according to claim 1 wherein the amount of amlodipine besilate is 14 mg.

20. The solid composition according to claim 1 in the form of a tablet wherein the total weight of the tablet is 500 mg.

21. The process according to claim 11 wherein the pre-lubricating step comprises the mixing of the blend of step iv) 20 min before doing the lubricating step.

\* \* \* \* \*

UNITED STATES PATENT AND TRADEMARK OFFICE
CERTIFICATE OF CORRECTION

PATENT NO. : 9,173,848 B2  Page 1 of 1
APPLICATION NO. : 13/381534
DATED : November 3, 2015
INVENTOR(S) : Khullar et al.

It is certified that error appears in the above-identified patent and that said Letters Patent is hereby corrected as shown below:

On the Title Page:

Item (75): please replace

"Inventors: Praveen Khullar, Goa (IN); Vinay Kolhe, Goa (IN); Amol Kulkarni, Goa (IN); Shirishbhai Patel, Goa (IN); Yashwant Phadke, Goa (IN); D Saravanan, Goa (IN); Mansing Shingte, Goa (IN)" with --Inventors: Praveen Khullar, Goa (IN); Vinay Kolhe, Goa (IN); Amol Kulkarni, Goa (IN); Shirishbhai Patel, Goa (IN); Yashwant Phadke, Goa (IN); Saravanan Devarajan, Goa (IN); Mansing Shingte, Goa (IN)--.

In the Claims:

At column 14, claim number 11, line numbers 46-47: please replace "iv. mixing the irbesartan granules of step iii with the amlodipine besilate blend of step iii;" with --iv. mixing the irbesartan granules of step ii) with the amlodipine besilate blend of step iii);--.

Signed and Sealed this
Third Day of May, 2016

Michelle K. Lee
*Director of the United States Patent and Trademark Office*